United States Patent
Hartmann et al.

(10) Patent No.: US 6,858,729 B2
(45) Date of Patent: Feb. 22, 2005

(54) ORGANIC RED ELECTROLUMINESCENT CHROMOPHORES, METHOD FOR THE PRODUCTION AND USE THEREOF

(75) Inventors: Horst Hartmann, Merseburg (DE); Andreas Kanitz, Höchstadt (DE); Wolfgang Rogler, Möhrendorf (DE); Kay Steffen, Eichstetten a. Kaiserstuhl (DE)

(73) Assignee: SIEMENS Aktiengesellschaft, Munich (DE)

( * ) Notice: Subject to any disclaimer, the term of this patent is extended or adjusted under 35 U.S.C. 154(b) by 0 days.

(21) Appl. No.: 10/469,129

(22) PCT Filed: Feb. 15, 2002

(86) PCT No.: PCT/DE02/00550

§ 371 (c)(1),
(2), (4) Date: Feb. 2, 2004

(87) PCT Pub. No.: WO02/068431

PCT Pub. Date: Sep. 6, 2002

(65) Prior Publication Data

US 2004/0116700 A1 Jun. 17, 2004

(30) Foreign Application Priority Data

Feb. 27, 2001 (DE) .......................................... 101 09 333

(51) Int. Cl.$^7$ .......................... C07D 498/22; F21S 4/00; H01J 1/62

(52) U.S. Cl. .......................... 544/69; 362/800; 313/503; 313/504

(58) Field of Search .......................... 544/69; 362/800; 313/503, 504

(56) References Cited

U.S. PATENT DOCUMENTS 5,028,643 A * 7/1991 Jaffe ........................... 524/90

FOREIGN PATENT DOCUMENTS

| DE | 100 02 424 | 7/2001 |
|----|------------|--------|
| DE | 100 38 436 | 3/2002 |
| EP | 0 969 531 | 1/2000 |
| EP | 1 074 602 | 2/2001 |
| WO | WO 94 19355 | 9/1994 |
| WO | WO 01/53287 | 7/2001 |
| WO | WO 02/12212 | 2/2002 |

* cited by examiner

Primary Examiner—Charanjit S. Aulakh
(74) Attorney, Agent, or Firm—Young & Thompson

(57) ABSTRACT

The invention relates to chromophores exhibiting semiconductive properties, the production and use thereof as luminophores in organic light-emitting diodes (OLEDs) and organic solar cells. The invention more specifically relates to highly condensed boron complex compounds wherein the boron atoms have improved processability, solubility and the fluorescence quantum efficiency is increased by building up by spirocenters.

6 Claims, No Drawings

ORGANIC RED ELECTROLUMINESCENT CHROMOPHORES, METHOD FOR THE PRODUCTION AND USE THEREOF

CROSS REFERENCE TO RELATED APPLICATIONS

This is the 35 USC 371 National Stage of International Application PCT/DE02/00550 filed on Feb. 15, 2002, which designated the United States of America.

FIELD OF THE INVENTION

The invention relates to chromophores with semiconducting properties, their production and use as luminophores in organic light emitting diodes (OLEDS) and organic solar cells.

BACKGROUND OF THE INVENTION

In patent applications DE 10002423 and DE 10002424 as well as in applications DE 10038436 and DE 10038437 (all hitherto unpublished), new organic semiconductor materials have already been presented which exhibit high fluorescence and form glaseous phases also as solids.

The new semiconductor materials are suitable for covering the long-wavelength emitting spectral range (orange to red) and belong to the "small molecules", although they can also be processed by spin coating. The materials are suitable both for the construction of organic light emitting diodes (OLEDs) and for the construction of organic photovoltaic elements and finally also for the construction of other organic electronic devices, these being able to be used in both hole and electron transfer layers and in emitter layers.

The materials are preparatively accessible in high yields and are obtained from 2-N,N-di(het)aryl aminothiophene and/or -thiazole derivatives.

There is additionally a need for new organic semiconducting and/or emitting materials for a wide range of applications in organic devices and light emitting diodes.

The new materials according to the invention extend the range of intensively luminescent, boron complex based compounds claimed in application GR 200102309.

SUMMARY OF THE INVENTION

The object of invention is to create new, organic, thermally and photochemically stable, long-wavelength emitting electroluminescent compounds which can be used in light-emitting diodes and/or organic electronic devices, which are easily accessible preparatively and which lend themselves to mass production processes.

The subject matter of the invention is a highly condensed, boron complex based compound having the general structure I.

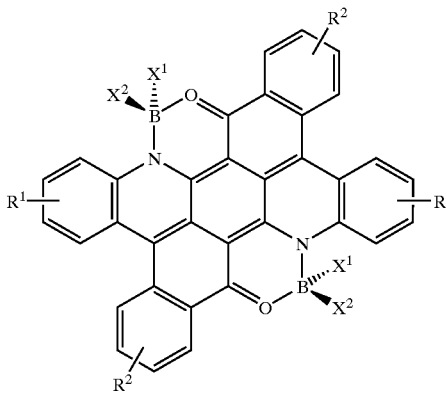

where $R^1$ and $R^2$, which can be the same or different independently of one another, stand for hydrogen, halogen, pseudohalogen, a nitrile and/or nitro group, an unsubstituted or alkyl, aryl and hetaryl substituted —$NR^3R^4$, —$OR^5$, —$PR^3R^4$ and —$SR^6$ and/or for a fused carbocyclic or heterocyclic ring, these groups possibly being branched or unbranched, containing 1 to 20 C atoms and containing various functional groups with N, O, S and/or P atoms in the event that $R^3$ to $R^6$ is alkyl;

where $X^1$ and $X^2$, which can be the same or different independently of one another, stand for halogen, preferably fluorine, alkyl- or aryloxy, the alkyl groupings possibly being branched or unbranched and containing 1 to 20 C atoms and various functional groups with N, O, S and/or P atoms or both jointly forming a cycle with the boron atom through an at least bidentate ligand, the at least bidentate ligand possibly having hydroxy and/or carboxylic acid groups and being preferably a diol, a hydroxy carboxylic acid or a dicarboxylic acid such as —$OC_2H_4O$—, —$OC_3H_6O$—, glycolate, lactate, tartrate, sylicylate, mandelate, benzilate, 1,2- or 2,3-hydroxynaphthoate, oxalate, malonate, alkylmalonate or dialkymalonate.

In the new long-wavelength emitting luminophores according to the invention, the tendency to crystallize is suppressed by the additional introduction of spiro elements so that the resulting three-dimensionality of the chromophores prevents or limits the stacking of the molecules to form crystals.

In the boron complex based compounds, the boron atoms act as spiro centers, promote the formation of glaseous phases of the system and prevent unwanted crystallization which causes a reduction in the system's fluorescent properties. The positive characteristics of spiro centers in organic semiconducting materials are already known.

Reaction scheme:

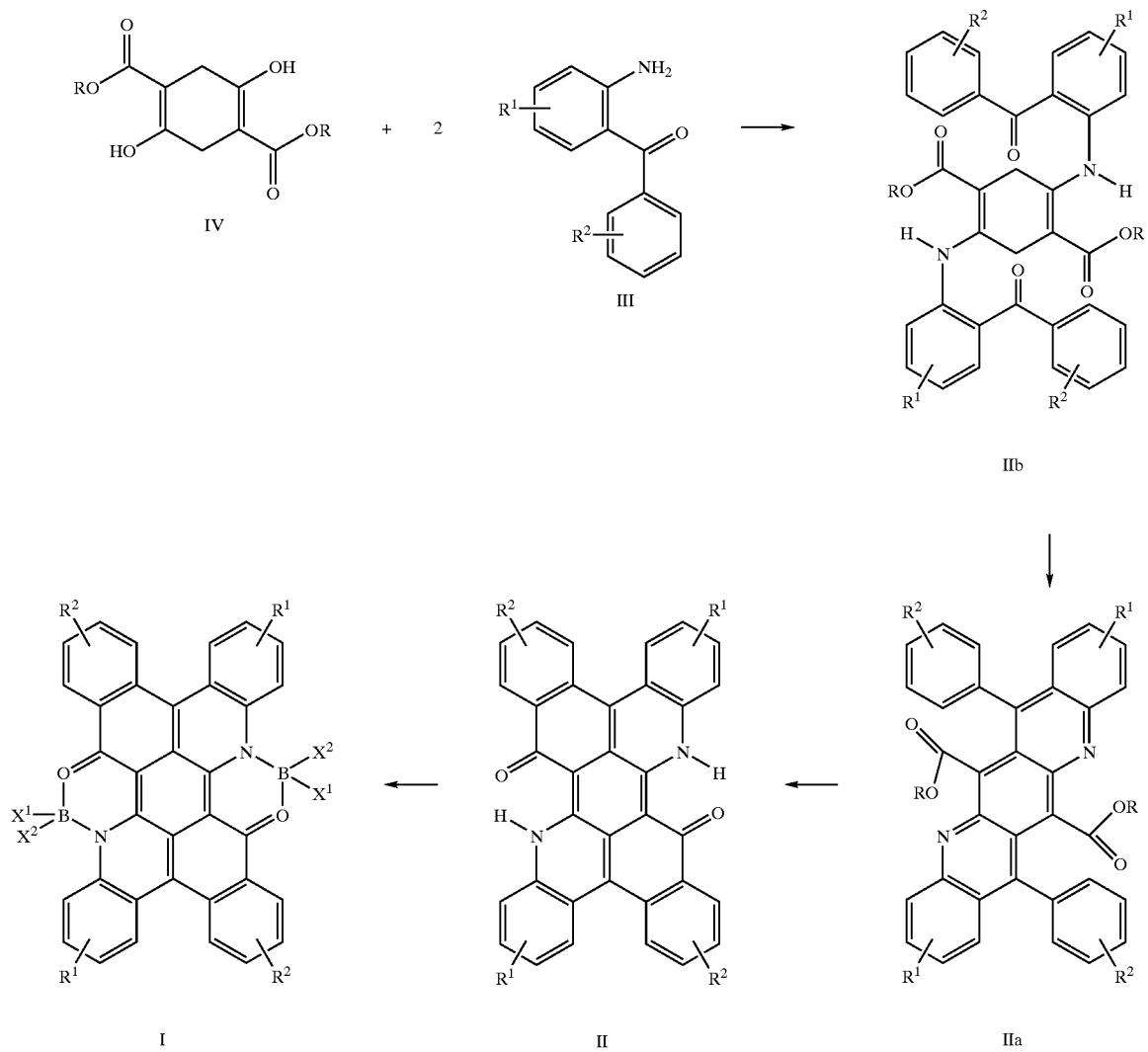

The highly condensed, boron complex based type I compounds according to the invention are produced from the type II compounds described in the literature (K. Kitahara, H. Nishi, J. Heterocyclic Chem. 25 (1988) 1063), in which the groups $R^1$ and $R^2$ as well as $X^1$ and $X^2$ have the abovementioned meanings, according to methods known in themselves, by their reaction with suitable boron compounds, possibly in the presence of a suitable coreagent and in the presence of a suitable solvent at elevated temperatures.

In particular, boron esters of carboxylic acids, preferably di- or oligocarboxylic acids and/or hydroxy-substituted carboxylic acids and complex adducts of boron halogenides with electron-donating solvents have been found to be suitable boron compounds for reacting with II.

Because of their high thermal and photochemical stability and their high-vacuum evaporability without decomposition at elevated temperatures as well as their ability to electroluminesce, the novel boron-complexed tetraaryl-diazaperylene heterocycles of type I are advantageously suitable as emitter materials for producing organic light-emitting diodes (OLEDs) and as a photochemically stable, photoactive material in organic solar cells and/or in other organic electronic devices. Thermal decomposition of these materials takes place only at temperatures >470° C.

DETAILED DESCRIPTION OF THE INVENTION

The following examples are intended to explain the invention in greater detail. Examples 1 to 3 describe the type II synthons required for producing the highly condensed, boron complex based type I compounds according to the invention. Examples 4–8 describe the production of the boron-complexed, highly condensed heterocycles from class I tetraaryl-diazaperylenes.

EXAMPLE 1

Synthesis of Diazaperylene Type II/1 $R^1=R^2=H$

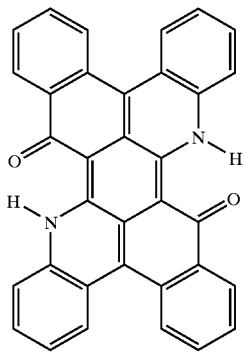

0.1 mol of 2-amino benzophenone III and 0.05 mol of succinylosuccinic acid diethyl ester IV are refluxed for 5 h in 50 ml of ethanol and 1 ml of hydrochloric acid. The product IIa precipitated from the reaction solution after cooling with a yield of 70% is drawn off, dried and then refluxed in 25 ml of 1-chloronaphthalene for 30 minutes. After cooling, the resulting product II/1 is isolated by suction and washed with approximately 200 ml of methanol for cleaning. Yield 70%; mp 405° C. The product has an absorption maximum of 648 nm and an emission maximum of 704 nm in ortho-dichlorobenzene.

EXAMPLE 2

Synthesis of Diazaperylene Type II/2 $R^1=Cl$ $R^2=H$

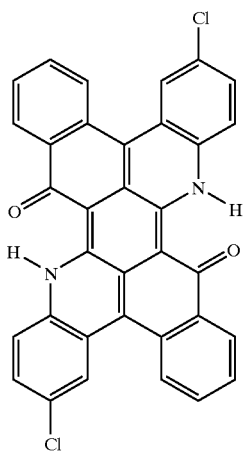

Similarly to Example 1, 0.1 mol of 2-amino-5-chlorobenzophenone III and 0.05 mol of succinylosuccinic acid diethyl ester IV are reacted in 50 ml of ethanol and 1 ml of hydrochloric acid. The product IIa precipitated from the reaction solution after cooling is drawn off, dried and then refluxed in 25 ml of 1-chloronaphthalene for 30 minutes. After cooling, the resulting product II/2 is isolated by suction and washed with approximately 200 ml of methanol for cleaning. Yield 82%; mp 470° C. The product has an absorption maximum of 649 nm and an emission maximum of 706 nm in o-dichlorobenzene.

EXAMPLE 3

Synthesis of Diazaperylene Type II/3 $R^1=R^2=Cl$

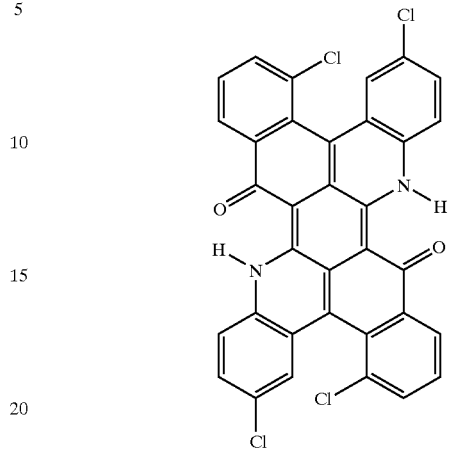

Similarly to Example 1, 0.1 mol of 2-amino-2',5-dichlorobenzophenone III and 0.05 mol of succinylosuccinic acid diethyl ester IV are reacted in 50 ml of ethanol and 1 ml of hydrochloric acid. The product IIa precipitated from the reaction solution after cooling is drawn off, dried and then refluxed in 25 ml of 1-chloronaphthalene for 30 minutes. After cooling, the resulting product II/3 is isolated by suction and washed with approximately 200 ml of methanol for cleaning. Yield 85%; mp>360° C. The product has an absorption maximum of 656 nm and an emission maximum of 708 nm in o-dichlorobenzene.

EXAMPLE 4

Synthesis of Boron-Complexed Diazaperylene Type I/1 $R^1=R^2=H$; $X^1=X^2=$—O—CO—CH$_3$

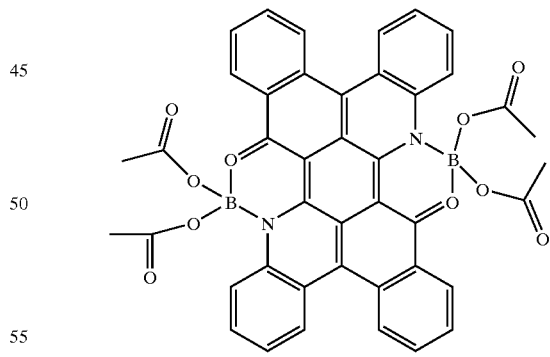

To a solution of boron acetate in an acetic acid/acetic anhydride mixture produced by dissolving 10 g of boric acid in 250 ml of acetic anhydride are added 0.05 mol of the starting compound II/1. This is refluxed until a virtually clear solution is obtained. After hot filtration it is allowed to cool and the resulting product I/1 is isolated by suction. Yield 95%; mp 380° C. The product has an absorption maximum of 567 nm and an emission maximum of 613 nm in acetone.

EXAMPLE 5
Synthesis of Boron-Complexed Diazaperylene Type I/2
R$^1$=Cl, R$^2$=H; X$^1$=X$^2$=—O—CO—CH$_3$

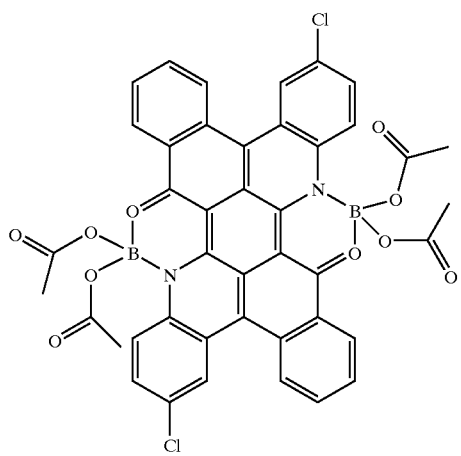

To a solution of boron acetate in an acetic acid/acetic anhydride mixture produced by dissolving 10 g of boric acid in 250 ml of acetic anhydride are added 0.05 mol of the starting compound II/2. This is refluxed until a virtually clear solution is obtained. After hot filtration it is allowed to cool and the resulting product I/2 is isolated by suction. Yield 92%; mp 379° C. The product has an absorption maximum of 581 nm and an emission maximum of 630 nm in acetone.

EXAMPLE 6
Synthesis of Boron-Complexed Diazaperylene Type I/3
R$^1$=Cl, R$^2$=H; X$^1$=X$^2$=—O—CO—C$_5$H$_{11}$ To a solution of boron capronate in a caproic acid/caproic anhydride mixture produced by dissolving 10 g of boric acid in 250 ml of caproic anhydride are added 0.05 mol of the starting compound II/2. This is refluxed until a virtually clear solution is obtained. After hot filtration it is allowed to cool and the resulting product I/3 is isolated by suction. Yield 90%; mp>360° C. The product has an absorption maximum of 582 nm and an emission maximum of 630 nm in acetone.

EXAMPLE 7
Synthesis of Boron-Complexed Diazaperylene Type I/4
R$^1$=Cl, R$^2$=H; X$^1$=X$^2$=—O—CO—C$_3$H$_7$

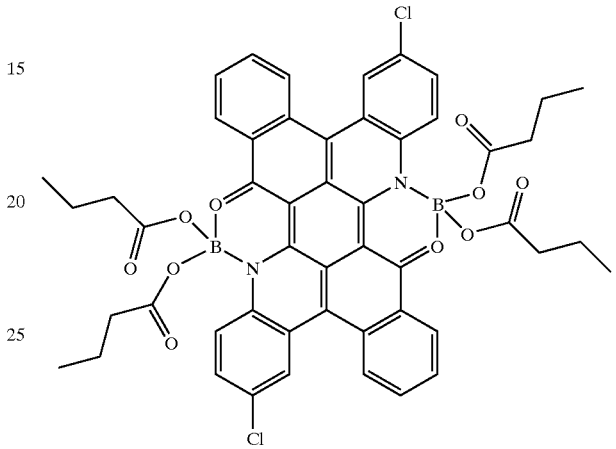

To a solution of boron butyrate in a butyric acid/butyric anhydride mixture produced by dissolving 10 g of boric acid in 250 ml of butyric anhydride are added 0.05 mol of the starting compound II/2. This is refluxed until a virtually clear solution is obtained. After hot filtration it is allowed to cool and the resulting product I/4 is isolated by suction. Yield 85%; mp>360° C. The product has an absorption maximum of 582 nm and an emission maximum of 630 nm in acetone.

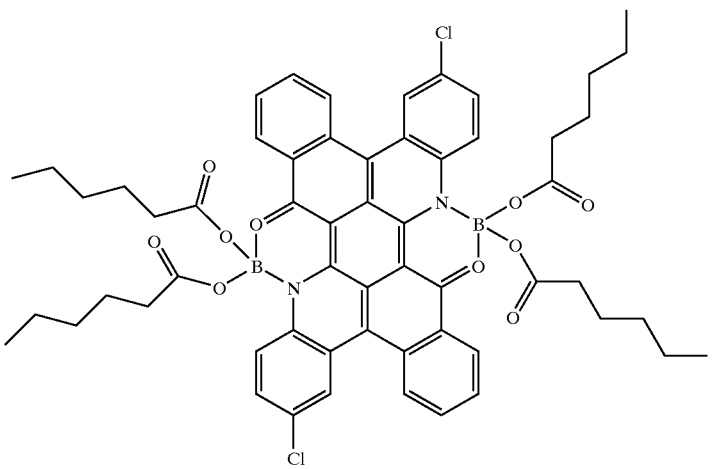

EXAMPLE 8

Synthesis of Boron-Complexed Diazaperylene Type I/5 $R^1=R^2=Cl$; $X^1=X^2=-O-CO-CH_3$

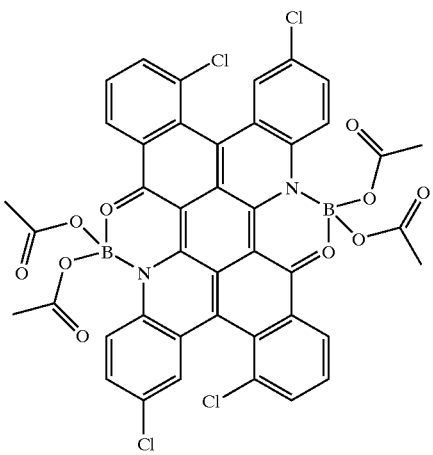

To a solution of boron acetate in an acetic acid/acetic anhydride mixture produced by dissolving 10 g of boric acid in 250 ml of acetic anhydride are added 0.05 mol of the starting compound II/3. This is refluxed until a virtually clear solution is obtained. After hot filtration it is allowed to cool and the resulting product I/5 is isolated by suction. Yield 82%; mp>360° C. The product has an absorption maximum of 573 nm and an emission maximum of 620 nm in acetone.

What is claimed is:

1. A compound of formula I,

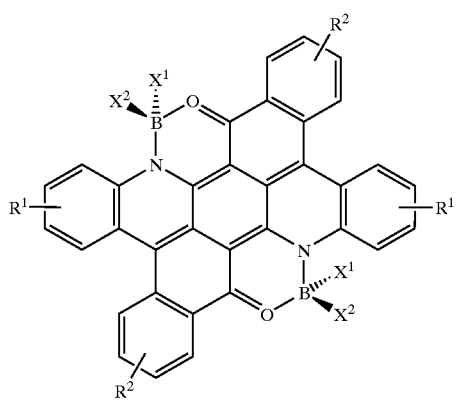

wherein $R^1$ and $R^2$, which can be the same or different independently of one another, stand for one of hydrogen; halogen; pseudohalogen; a nitrile and/or nitro group; an unsubstituted $-NR^3R^4$, $-OR^5$, $-PR^3R^4$ and $-SR^6$; $-NR^3R^4$, $-OR^5$, $-PR^3R^4$ or $-SR^6$ substituted with an alkyl, aryl, or an hetaryl; or $R^1$ and $R^2$ can be a fused carbocyclic or heterocyclic ring;

wherein $X^1$ and $X^2$, which can be the same or different independently of one another, stand for one of halogen, alkyl- and aryloxy, or both jointly forming a cycle with the boron atom through an at least bidentate ligand, the bidentate ligand having at least two places to bind a central atom, the ligand having hydroxy and/or carboxylic acid groups and being a diol, a hydroxy carboxylic acid or a dicarboxylic acid that is one of $-OC_2H_4O-$, $-OC_3H_6O-$, glycolate, lactate, tartrate, sylicylate, mandelate, benzilate, 1,2- or 2,3-hydroxynaphthoate, oxalate, malonate, alkylmalonate or dialkymalonate.

2. A method for preparing the compound according to claim 1, comprising reacting diazaperylene II with a compound selected from the group consisting of at least one boron ester of either a carboxycyclic acid or a di- or oligocarboxylic acid or a di- or oligocarboxycylic acid or a hydroxy substituted carboxylic acid and a complex adduct of a born halogenide to obtain the compound according to claim 1.

3. The method according to claim 2, wherein the reaction takes place in at least one electron-donating solvent.

4. A method of preparing an organic light-emitting diode, which comprises adding a compound according to claim 1 as an organic semiconducting emitter material in a hole and/or electron transfer layer of said organic light-emitting diode (OLED).

5. A method of preparing an organic electronic device, which comprises adding compound I according to claim 1 as an organic semiconducting material in said organic electronic device.

6. A method of producing an organic solar cell, which comprises adding compound I according to claim 1 as a photochemically stable, photoactive material in said organic solar cell.

* * * * *